United States Patent [19]
Buchmann et al.

[11] Patent Number: 5,661,294
[45] Date of Patent: Aug. 26, 1997

[54] PROCESS AND APPARATUS FOR THE OPTICAL INSPECTION OF A TRANSPARENT REGION OF A CONTAINER, IN PARTICULAR THE MOUTH REGION

[75] Inventors: Christa Buchmann, Birmensdorf; Karl-Georg Burri, Oberrieden, both of Switzerland

[73] Assignee: Elpatronic AG, Zug, Switzerland

[21] Appl. No.: 706,300

[22] Filed: Aug. 30, 1996

Related U.S. Application Data

[63] Continuation of Ser. No. 349,526, Dec. 5, 1994, abandoned.

[30] Foreign Application Priority Data

Dec. 6, 1993 [CH] Switzerland ............ 03 675/93
Aug. 25, 1994 [CH] Switzerland ............ 02 602/94

[51] Int. Cl.⁶ ..................................... G01N 9/04
[52] U.S. Cl. .................. 250/223 B; 356/240; 356/428; 209/526
[58] Field of Search ............. 250/223; 356/240, 356/428; 209/524–526

[56] References Cited

U.S. PATENT DOCUMENTS

| | | | |
|---|---|---|---|
| 4,083,637 | 4/1978 | Ellinger et al. | 356/240 |
| 4,367,405 | 1/1983 | Ford | 250/223 B |
| 4,428,673 | 1/1984 | Yoshida | 356/240 |
| 4,731,649 | 3/1988 | Chang et al. | 356/240 |
| 4,807,995 | 2/1989 | Dassler et al. | 250/223 B |
| 5,030,823 | 7/1991 | Obdeijn | 250/223 B |
| 5,072,107 | 12/1991 | Apter . | |
| 5,214,713 | 5/1993 | Juvinall | 250/223 B |
| 5,216,239 | 6/1993 | Yoshida | 250/223 B |
| 5,233,186 | 8/1993 | Ringlien | 250/223 B |

FOREIGN PATENT DOCUMENTS

| | | | |
|---|---|---|---|
| 0 047 936 | 3/1982 | European Pat. Off. | G01N 21/90 |
| 0 060 918 | 9/1982 | European Pat. Off. | G01N 21/90 |
| 0 209 077 | 1/1987 | European Pat. Off. | G01N 21/90 |
| 0 426 968 | 5/1991 | European Pat. Off. | G01N 21/90 |
| 52-022983 | 2/1977 | Japan . | |
| 55-149830 | 11/1980 | Japan . | |
| 59-78965 | 5/1984 | Japan . | |
| 60-098340 | 6/1985 | Japan . | |
| 61-296244 | 12/1986 | Japan . | |
| 62-012845 | 1/1987 | Japan . | |
| 63-72552 | 5/1988 | Japan . | |
| 64-69937 | 3/1989 | Japan . | |
| 3-502138 | 5/1991 | Japan . | |
| 3-150502 | 6/1991 | Japan . | |
| WO9002937 | 3/1990 | WIPO | G01N 21/90 |

*Primary Examiner*—Stephone Allen
*Attorney, Agent, or Firm*—McCormick, Paulding & Huber

[57] ABSTRACT

To photograph the mouth region of a bottle, a light-emitting surface is arranged below the mouth region to be photographed. The light-emitting surface is illuminated by means of an illuminating device and the image of the illuminated mouth region is directed to a camera by a mirror arrangement (5,6,11). The light-emitting surface makes it possible to image the mouth region in transmitted light, facilitating detection of defects and soiling in the mouth region from the interpretation of the image recorded by the camera.

29 Claims, 13 Drawing Sheets

5,661,294

PROCESS AND APPARATUS FOR THE OPTICAL INSPECTION OF A TRANSPARENT REGION OF A CONTAINER, IN PARTICULAR THE MOUTH REGION

This is a continuation of application Ser. No. 08/349,526 filed on Dec. 5, 1994 now abandoned.

BACKGROUND OF THE INVENTION

The invention relates to processes for the optical inspection of a transparent region of a container, in particular the mouth region of a bottle, in which an image of the region which can be observed by at least one camera is produced. The invention also relates to apparatus for carrying out the processes.

A process and an arrangement for optical inspection of a rotationally symmetrical body, in particular for inspecting bottle mouths with a screw thread, are known from the document EP-A-47936. Another apparatus for inspecting the mouth region of bottles which is intended to overcome drawbacks of the apparatus according to the first-mentioned document is known from the document EP-B-209077. However, a drawback of both forms of apparatus is that the bottle mouth region is illuminated by incident light, which makes inspection of the image produced at the camera difficult, as only relatively small differences in brightness result between clean undamaged bottles on the one hand and soiled and/or damaged bottles on the other hand. This is a particular problem in the case of bottles with screw threads which are provided with vertical slots (vent-slots). This applies eg. to returnable PET bottles.

SUMMARY OF THE INVENTION

It is an object of the present invention to provide an improved process and an improved apparatus which do not have the said disadvantages and which can produce a more easily interpretable image of the bottle region to be inspected, by means of which soiling and damage are reliably and rapidly detectable.

In the process referred to above, this object may be achieved by arranging at least one essentially homogeneous light-emitting surface below the mouth region to be inspected, so that the mouth region can be observed in transmitted light.

In the above-mentioned apparatus the object may be achieved by providing an illuminating device, a reflecting surface which is illuminated thereby and which is arranged, as an essentially homogeneous light-emitting surface, below the region to be inspected, and a mirror arrangement by means of which the region can be observed by a camera.

In accordance with the invention, illumination of the region is inspected by transmitted light is effected by the homogeneous light-emitting surface below the region to be inspected. The effect of illumination by transmitted light is that sound bottles, and in particular clean vent-slots, show up brightly in the image. Soiling, on the other hand, shows up clearly as dark patches. The result is a marked improvement in the interpretability of the image recorded by the camera, giving improved, and in particular more rapid, inspection of the container.

A further object which is both additional to and separate from the above-mentioned object is that of directing the image of the bottle mouth to the camera or other light-sensitive arrangement in such a way that the whole of the mouth is clearly visible. This object can be achieved by a process with the features of claim 22 or 26 or 29 and with the apparatus for carrying out such a process.

BRIEF DESCRIPTION OF THE DRAWINGS

Embodiments of the invention will now be described in detail by way of example with reference to the accompanying drawings, in which.

DESCRIPTION OF THE PREFERRED EMBODIMENTS

Figure 1:
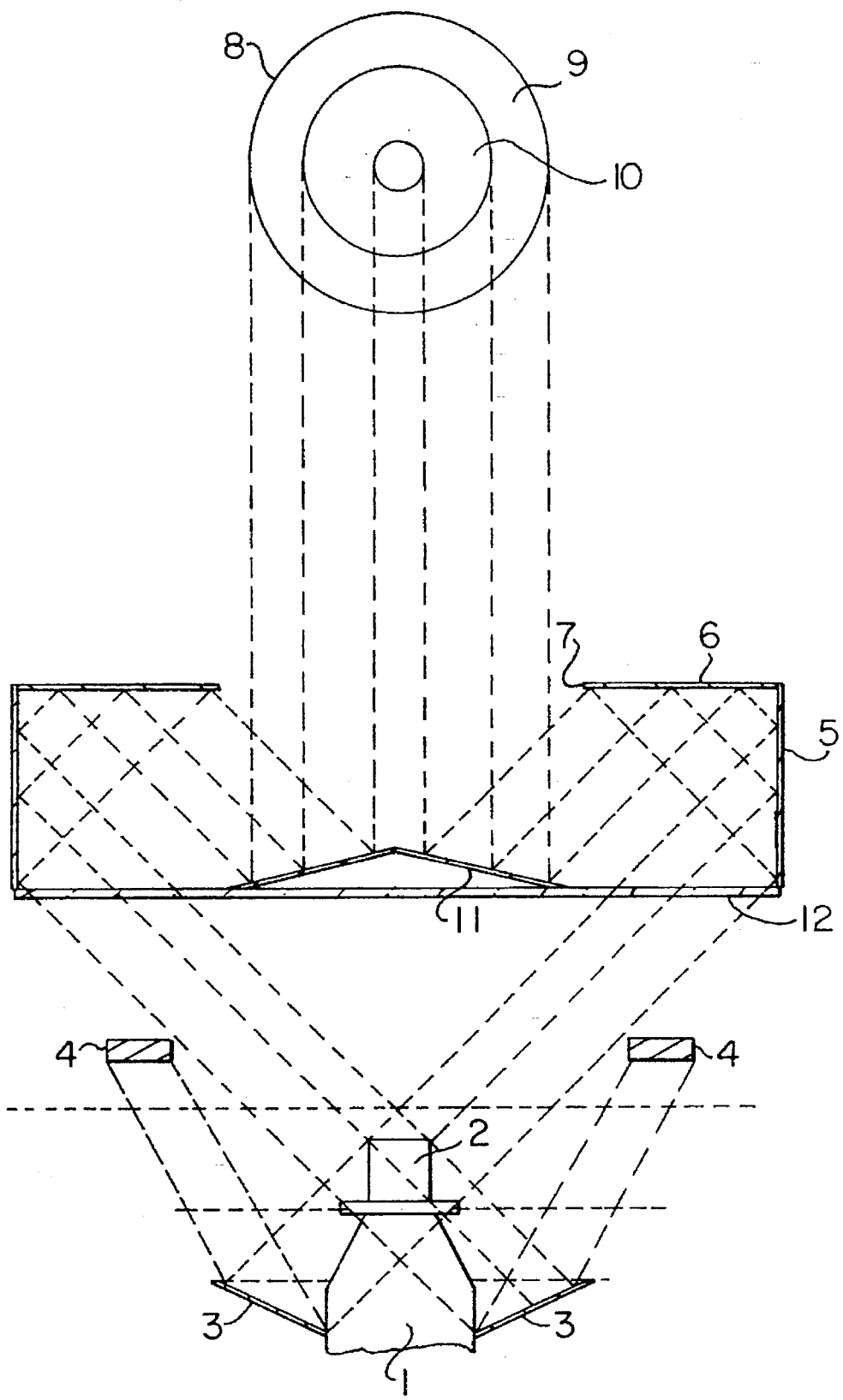
FIG. 1 schematically shows a first embodiment of apparatus according to the invention, in partly cut-away elevation.

FIG. 1 schematically illustrates a bottle 1 (only part of which is shown) with its mouth region 2. The mouth region 2 is usually provided with a screw thread (not shown). Vertical slots, called vent-slots, may be provided in the screw thread. Such slots are present eg. on PET bottles. A light-emitting surface 3 surrounding the container 1 is provided below the mouth region. In the example shown, the light-emitting surface 3 is formed as a reflecting surface, eg.

as a white surface, which is lit by an annular lighting source 4. This annular lighting source 4 may comprise eg. a flash lamp or an array of light-emitting diodes with pulsed operation.

Above the container 1, a mirror arrangement with mirrors 5,6 and 11 is provided. The mirror arrangement is closed off with a glass plate 12 on the side towards the container and on its opposite side has an opening 7 towards a camera which is not shown in the drawing. In FIG. 1, in place of the camera, the image to be observed by the camera is represented above the opening 7, to assist the explanation of the invention. In the illustrated example, the above-mentioned mirror arrangement comprises a cylindrical mirror 5 and an annular mirror 6 which adjoins this cylindrical mirror 5 and which also forms the opening 7. A conical mirror 11 with a reflecting external surface is arranged inside the cylindrical mirror 5. In FIG. 1, the resulting ray path to the image represented above the opening 7 is indicated by dotted and broken lines. As a result, in a manner known in itself, the image 8 is formed which is indicated above the opening and which represents in the form of rings both the exterior 10 of the screw thread and the interior 9 of the screw thread. This yields the known advantage that all the information necessary for the inspection is contained in one image and only one camera is needed.

According to the invention, however, in contrast with known arrangements, the container is illuminated by means of the light-emitting surface 3, which is a reflecting surface in the illustrated example, but which may also be a light-radiating surface. Illumination with the light-emitting surface means that, in contrast with the known arrangements, the container region to be inspected is observed in transmitted light. In particular this yields the major advantage that the background is light, so that unblemished, clean bottles, and in particular clean vent-slots, appear light in the image, while soiling appears in the form of dark patches. Compared with observation in incident light as in the past, with the bottle appearing in front of a dark or indistinct background, this makes for easier interpretation of the image recorded by the camera. The three-mirror arrangement affords the additional advantage, compared with a single conical mirror, that regions which are of interest (that is, on the interior) appear at the edge of the picture, where resolution is higher than at the centre of the picture, owing to the geometry of the light transmission system. The number of pixels in the overall picture can therefore be reduced.

Figure 2:
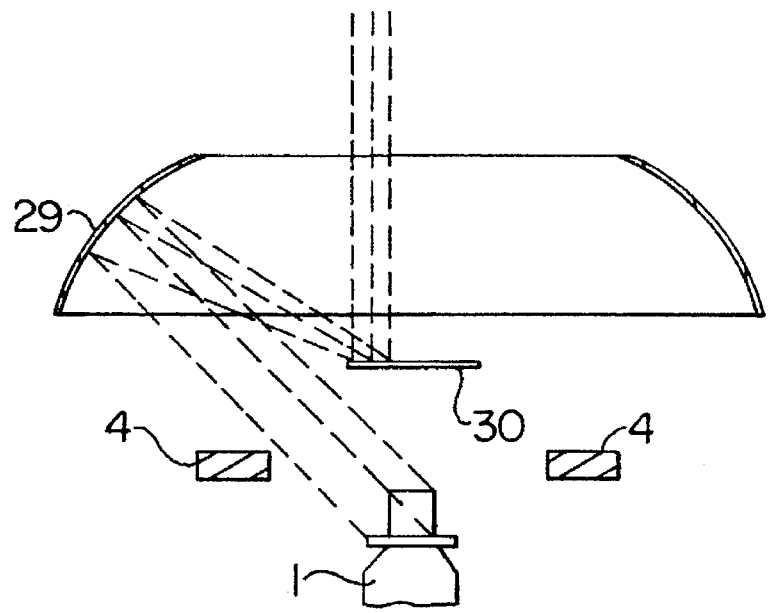
FIG. 2, likewise in schematic form, shows an embodiment of the mirror arrangement.

FIG. 2 shows another embodiment of the mirror arrangement. In this embodiment a curved mirror 29 is arranged above a plane mirror 30. The curved mirror may be spherical or parabolic.

Figure 3:
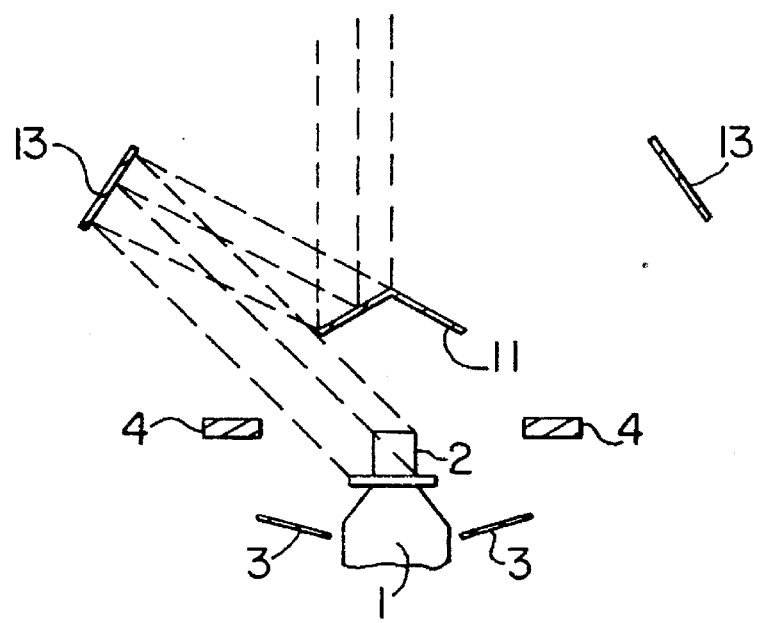
FIG. 3, likewise in schematic form, shows another configuration of the mirror arrangement.

FIG. 3 shows a further embodiment of the mirror arrangement, in this case with a mirror 13 in the form of a frustum of a cone, and a conical mirror 11. The same result can be obtained with the mirror arrangements shown in FIG. 2 and FIG. 3 as with the mirror arrangement shown in FIG. 1. In FIGS. 2 and 3, the container with the light-emitting surface 3 and light source 4 and ray paths are only partially shown.

Figure 4:
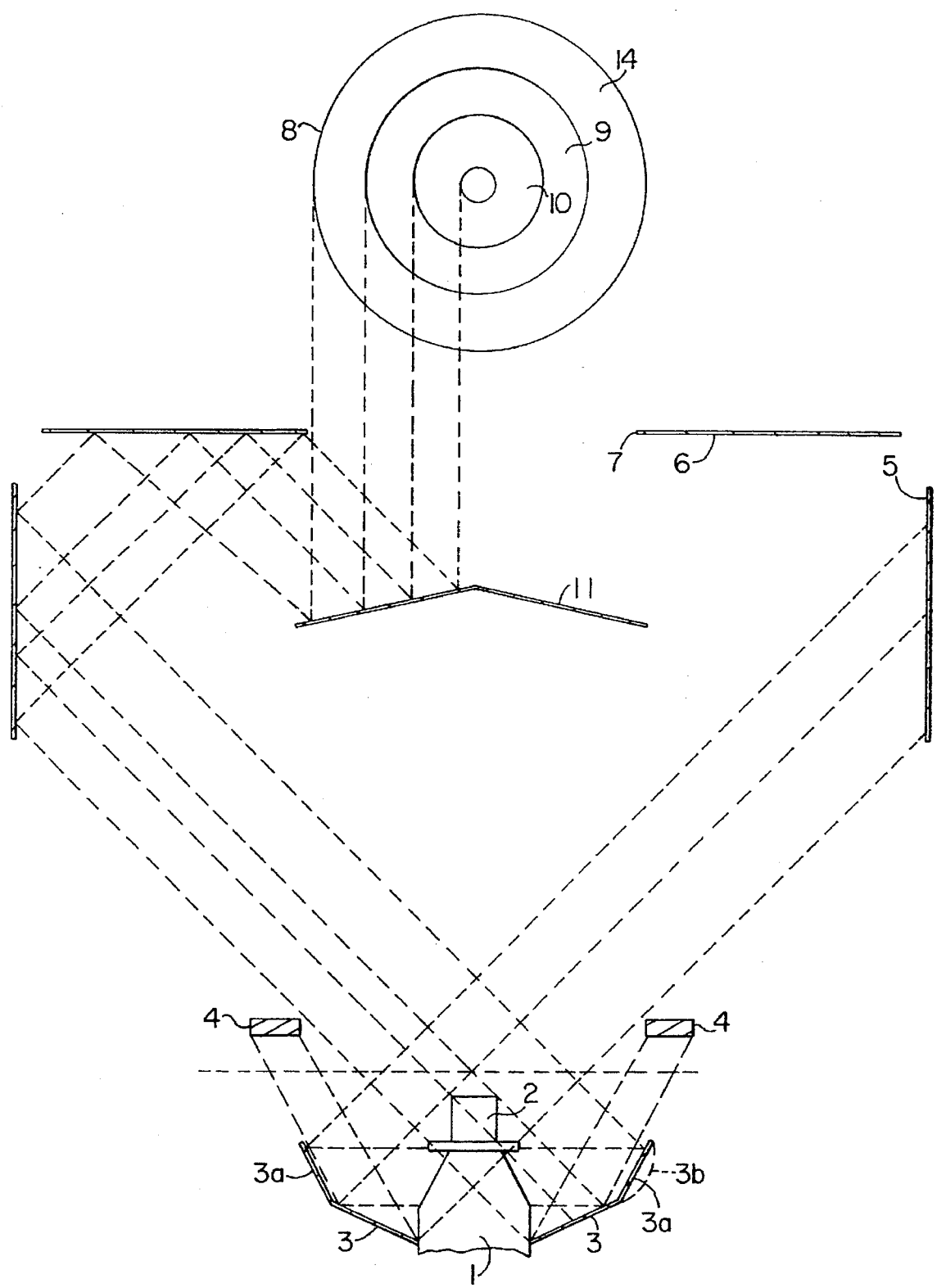
FIG. 4 shows a further embodiment of apparatus according to the invention, again in partly cut-away elevation.

FIG. 4 shows another embodiment of the invention, the same reference numbers being used to designate the same elements as before. In the embodiment shown in FIG. 4, the light-emitting surface 3 formed as a reflecting surface has an adjoining additional reflecting surface 3a surrounding the container. This reflecting surface 3a is not directly lit by the illuminating device 4, but reflects incident light and transmitted light (or transmitted light only, if a corresponding shield is provided) reflected from the part of the container below the mouth, or as the case may be transmitted light from the white surface opposite e.g., the portion of the reflecting surface positioned on the opposite side of the container (diffuse light) and incident light. The reflecting surface 3a is formed eg. as a conical mirror, as illustrated in the drawing.

This extension of the light-emitting surface by an adjoining reflecting surface makes it possible, in the example shown, to include the region below the mouth (haze area) in the image 8. In the optical image 8 which has been indicated above the opening 7 in place of the camera for the sake of clarity, the region under the mouth is visible as a ring 14. In this way, a less critical region of the container can additionally be observed in incident light and transmitted light, or in transmitted light only. Usually, less resolution of the image is needed in the region 14 than in the screw-thread regions. Therefore, instead of the conical mirror 3a, eg. a curved mirror can be provided, as indicated by the curved outline of the mirror 3b in the right-hand half of FIG. 4. This mirror configuration yields a narrower ring 14. The mirror 3a, 3b can be made semi-transparent in order to give a more uniform distribution of brightness in the image 8. It is also possible to provide a number of individual mirrors so that only partial images of the haze area are projected.

Figure 5:
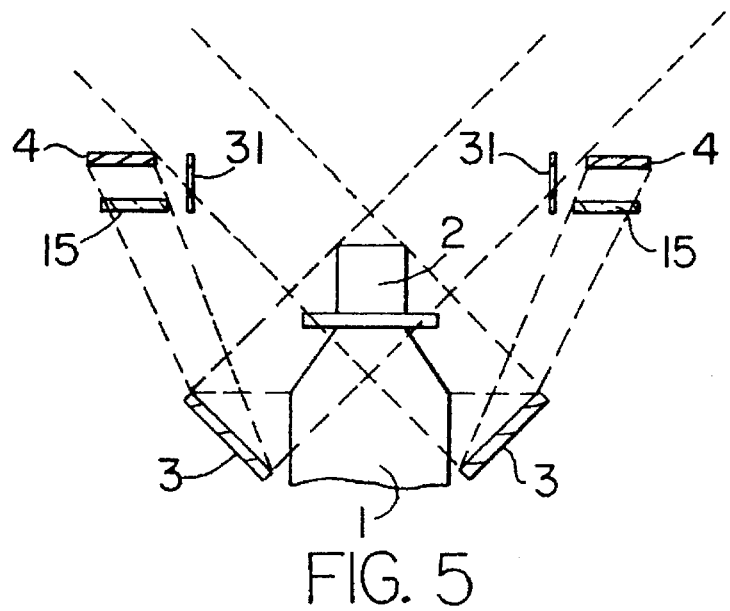
FIG. 5 shows one configuration of illuminating device employed in the apparatus.

FIG. 5 shows only a part of the arrangement in comparison with the previous drawings: that is to say, the mirrors and the resulting image (and camera) shown in these drawings are omitted from FIG. 5. The arrangement shown in FIG. 5 can, however, be combined with each of the mirror arrangements which have so far been illustrated. FIG. 5 additionally shows how a diffusion plate 15 can be provided on the illuminating device 4, eg. on the LED array or flash lamp. In this case, for example, a mirror surface can be provided instead of the reflecting white surface forming the light-emitting surface 3. For a homogeneous distribution of light over the light-emitting surface 3, the white surface is, however, preferred. Here again, instead of the construction shown, the light-emitting surface 3 can take the form of a light-radiating surface formed eg. by annular flash lamps or annular LED arrays, likewise with diffusion plate fitted. A shield 31 can additionally be provided to prevent reflections. With the shield fitted, observation is by transmitted light only; without the shield, by both transmitted and incident light.

Figure 6:
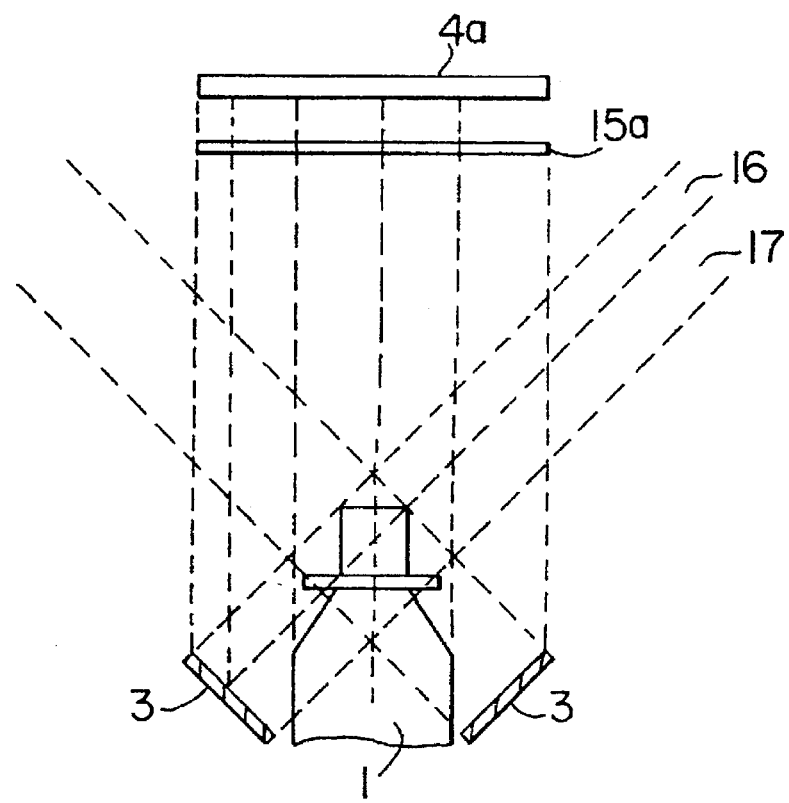
FIG. 6 shows another configuration of the illuminating device.

FIG. 6 shows another arrangement of an illuminating device and of the light-emitting surface 3. In this case the illuminating device consists of a circular LED array 4a or flash lamp with a diffusion disk 15a. This circular illuminator is arranged perpendicularly above the container and illuminates the white surface 3. With this arrangement there is combined observation of the mouth region in both incident and transmitted light. This is represented by the ray paths 16 and 17. The ray path 16 carries illumination of the interior of the screw thread by transmitted light, and the ray path 17 carries illumination of the exterior of the screw thread by incident light and transmitted light. The mirror arrangement is not shown in FIG. 6. Any desired mirror arrangements which divert the beams shown to the camera in the manner which has already been described can be used. The light-emitting diode arrangement shown is inductively powered in the illustrated example, since power leads would have to pass through the ray paths.

Figure 7:
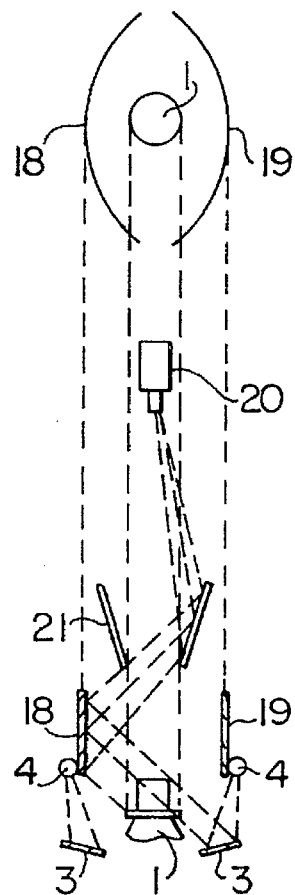
FIG. 7 shows a schematic representation of another embodiment of apparatus according to the invention with parabolic mirrors.

FIG. 7 shows another embodiment of the invention, likewise in schematic and partly cut-away elevation. The container to be inspected and the light-emitting surface 3 with illuminator 4 are again seen in schematic and partly cut-away elevation. The mirror arrangement in this embodiment consists of two parabolic mirrors 18,19, which are additionally depicted in plan view above the camera 20 in order to show their shape more clearly. Behind the parabolic mirrors 19, flat mirrors 21 are arranged, to deflect the rays from the parabolic mirrors towards the camera 20, as is shown for the ray path from the right-hand light-emitting surface 3. Two views of the screw thread, which is both internally and externally observable, are formed. The parabolic mirrors have the advantageous effect of stretching the image (the circle becomes a rectangle). This requires a camera with fewer image points. Also, the image can be transmitted in linear form.

Figure 8:
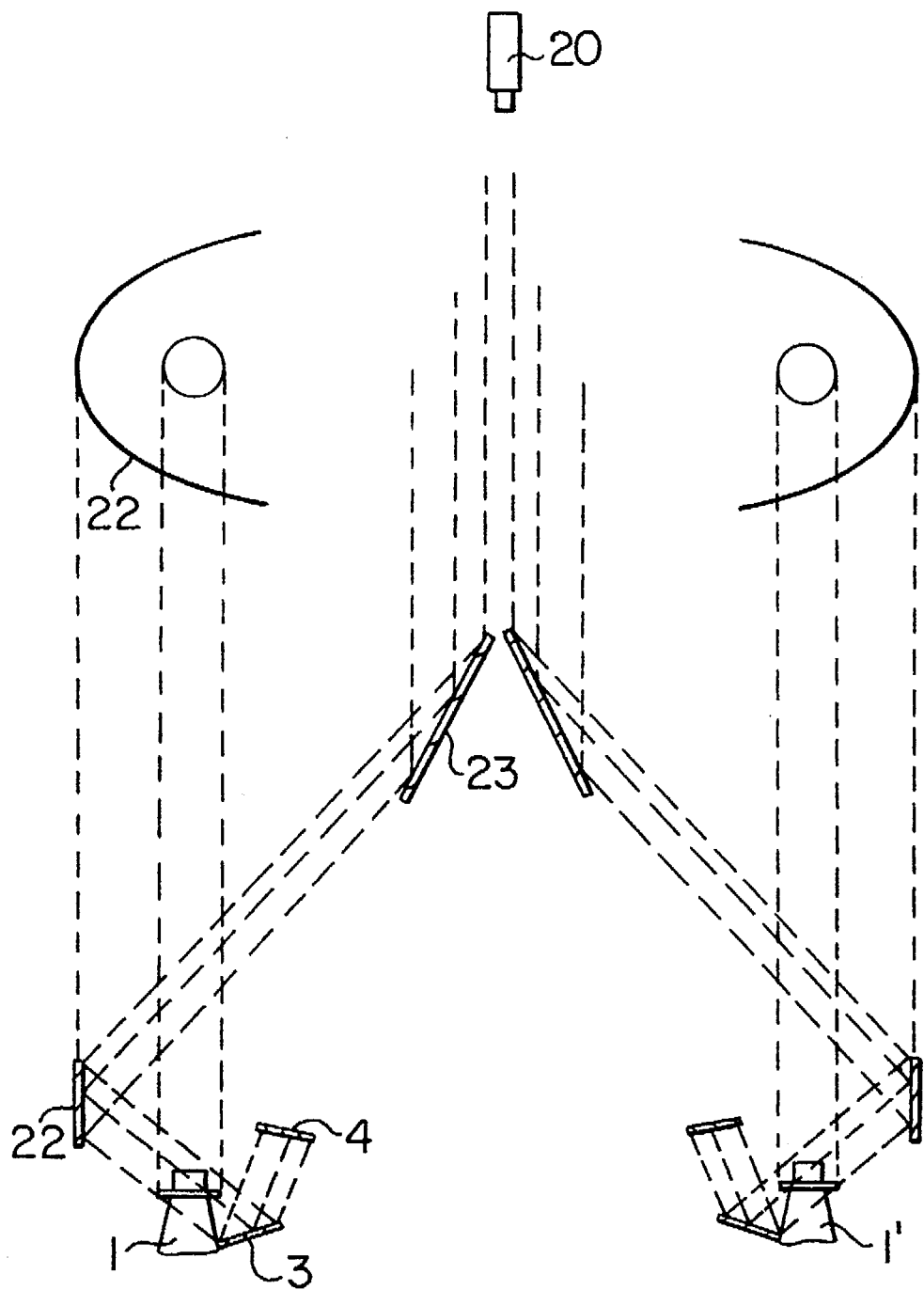
FIG. 8 also shows an embodiment of apparatus according to the invention with parabolic mirrors.

FIG. 8 shows another embodiment of the apparatus comprising a parabolic mirror. In this embodiment a parabolic mirror 22 with high curvature is provided, as is additionally illustrated in the figure in plan view. With this embodiment shown in FIG. 8, two different containers 1,1' are inspected simultaneously, and their mouth region is portrayed in an image recorded by the camera 20. However, the image does not portray the whole of the mouth region of either container 1,1'. For this reason, in the example shown, it is necessary for each container to pass through both inspection stations. Accordingly, the container 1 is first observed in the inspection station shown on the left of the diagram, and the half-image obtained is stored in memory or directly evaluated. Later, the container 1 is positioned in the inspection station illustrated on the right of the drawing and the mouth region not previously inspected is recorded in a later half-image. For the evaluation, both half-images are called into play (assuming they can be stored) in order to detect a defect or soiling of the bottle. In these arrangements with parabolic mirrors, two or more cameras may be provided (FIG. 8), and two or more parabolic mirrors may be provided (FIG. 7 and FIG. 8).

Figure 9:
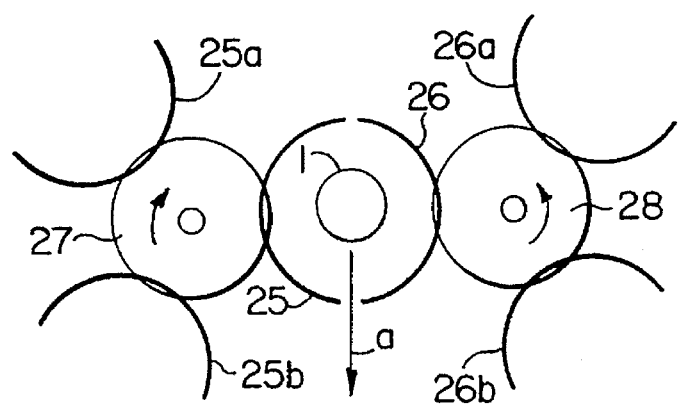
FIG. 9 shows, in schematic form, a system for locating the light-emitting surface with a container.

FIG. 9 shows, in highly schematic form, in plan view, one possible way of placing the light-emitting surface 3 on the container, it being assumed that the container is moving on a conveyor system, as indicated by the arrow a. The light-emitting surface surrounding the container is in this case formed by two half-surfaces 25,26 (or as the case may be 25a and 26a, or 25b and 26b) mounted on two rotating turntables 27 and 28. These turntables 27 and 28 rotate synchronously at a speed which is matched to that of the conveyor carrying the container 1 so that the two half-surfaces join together to form the light-emitting surface as they pass the location of the camera and/or mirror arrangement and illuminator. As soon as this occurs, the container is momentarily illuminated by the illumination device 4 and the picture is taken by the camera. As the container 1 continues on its way, the two halves 25,26 of the light-emitting surface 3 swing clear of the path of the container. The next container on the conveyor is then encircled by the halves 25a and 26a, whereupon the illumination, the taking of the picture and the pivoting-clear again ensue. The next container is then encircled by the halves 25b and 26b; the next container after that, by the halves 25 and 26 again; and so forth.

Figure 10:
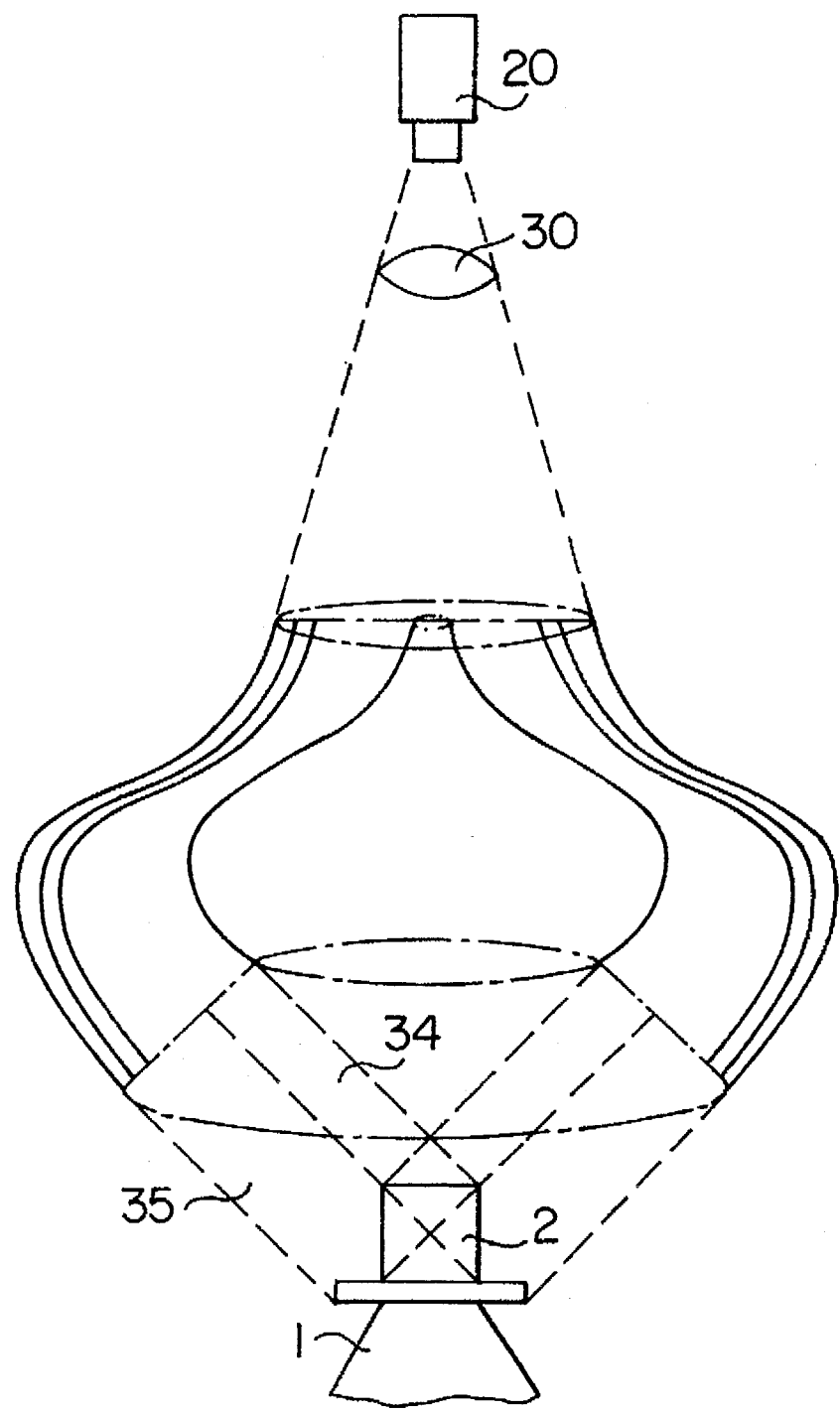
FIG. 10 schematically shows an arrangement for carrying out the process of the invention with optical fibres instead of mirrors.

FIG. 10 shows as an example an embodiment in which the mirror arrangement is replaced by a large number of optical fibres. In the figure, this is represented schematically, by a few fibres only. Different numbers of fibres may be provided for different regions needing to be imaged. The fibres may be arranged as schematically illustrated in FIG. 10, where the fibres receiving light from the bottle 1 by their end faces form a frustum of a cone, as indicated in the drawing. In this case, along a generating line of the truncated cone, eg. approx. 250 fibres are provided for the region 34 to be imaged (interior of the screw thread), and approx. 1600 fibres for the region 35 to be imaged (exterior of the screw thread). A lens 36 may be arranged in front of the camera 20. The light-emitting surface is not shown in FIG. 10 but if one is provided it may be formed as in the previous examples. Also there may be a linear arrangement of the light-emitting ends of the fibres. This has the advantage of yielding a simple image which can be processed linearly (as already mentioned in the case of the parabolic mirrors). A small lens may also be provided at the end of each fibre.

In each of the illustrated examples, the light-emitting surface and mirror and/or fibre arrangements are shown in conjunction. However, it must be emphasized that the mirror and/or fibre arrangements may also be used to good advantage independently of the light-emitting surface.

Figure 11:
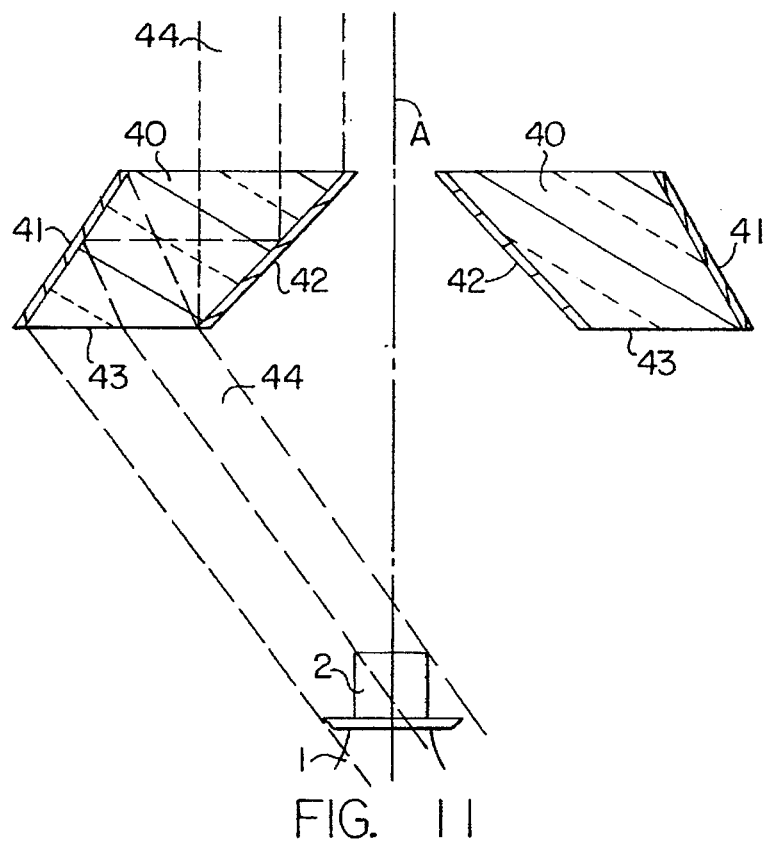
FIG. 11 shows an arrangement for imaging the bottle mouth by means of a body refracting the light ray.

FIG. 11 shows another possible way of imaging the mouth region 2 of a bottle 1 which is only partly shown. This figure schematically illustrates the ray path 44 from the bottle mouth 2 to an image recording arrangement not shown in the drawing, eg. a camera. Also omitted from the drawing is the illuminating device, which preferably operates with transmitted light as has already been described. In this case imaging is effected by means of a body 40 which consists of eg. glass and which refracts the rays. In the example shown, refraction of the rays occurs at the surface 43 of the body 40 and also at the upper face of the body, as the path of the rays is not precisely vertical, but is tilted towards the camera. The body 40 is shown in vertical section in FIG. 11, and is rotationally symmetrical about the axis A. In the example shown, the circumferential lateral faces 41 and 42 of the body 40 are mirrored so that the resultant ray path within the body 40 is as shown in the drawing. The advantage of such an arrangement lies in its robust construction and in the protection from soiling of the mirrored surfaces 41,42.

Figure 12:
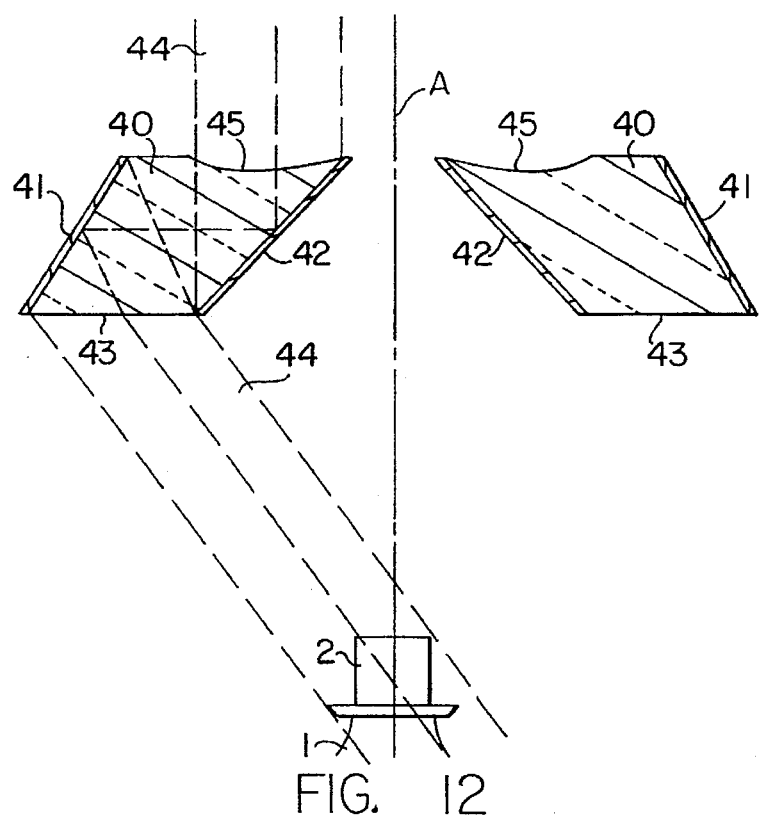
FIG. 12 shows an arrangement similar to that in FIG. 11, in which the body has a correcting curvature.

FIG. 12 shows an embodiment similar to that shown in FIG. 11, the same reference symbols being used to designate the same parts as in FIG. 11. A rotationally symmetrical refracting body 40 is again provided, and is provided with mirror surfaces 41,42. In this embodiment, a curved face 45 is provided on the side of the body 40 which faces the image recording apparatus, and the curvature serves to correct astigmatism. This enables imaging aberration to be corrected.

Figure 13:
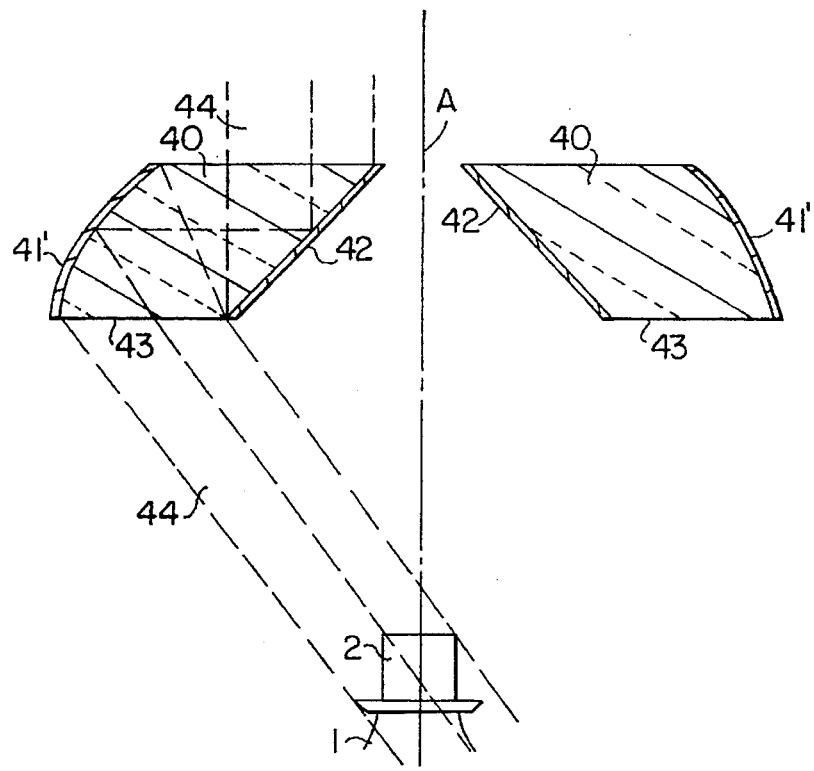
FIG. 13 shows another arrangement with correction.

FIG. 13 shows another variant similar to FIG. 11. This is also provided with the body 40, with a surface 43 at which refraction occurs. In the variant shown in FIG. 13, one mirrored face 41' is curved, again in order to correct the ray path and/or imaging to prevent aberration.

Figure 14:
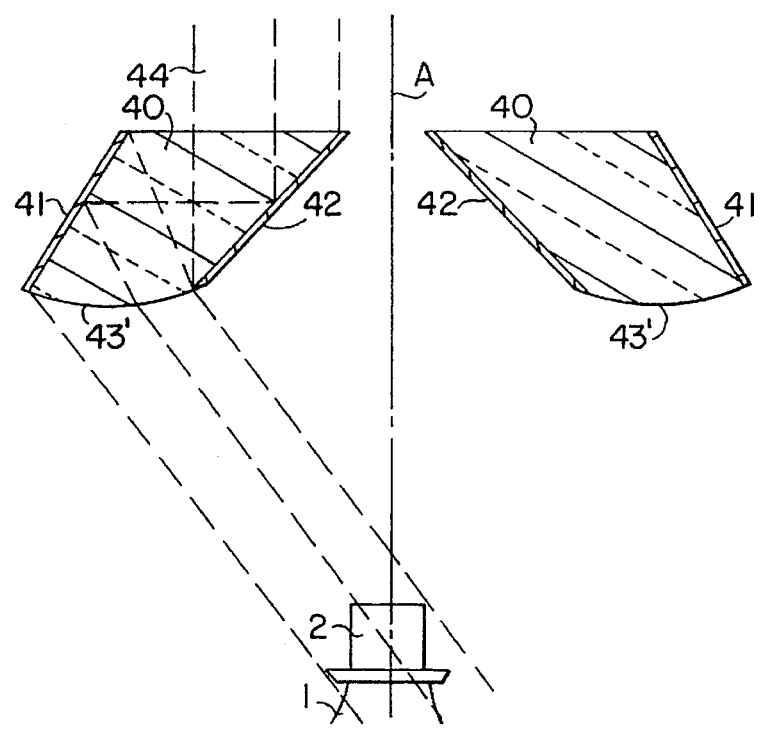
FIG. 14 shows another arrangement with correction.

FIG. 14 shows another embodiment in which the refracting face 43' of the body 40 is curved in order to bring about a correction of aberration. This embodiment also has the mirror faces 41,42, and the ray path is indicated at 44.

Figure 15:
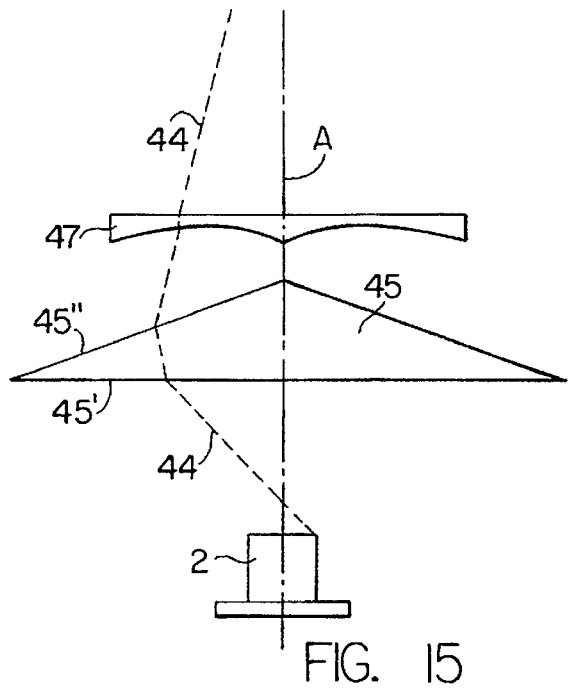
FIG. 15 shows an arrangement for imaging the bottle mouth by means of a prism and a correcting device.

FIG. 15 shows an embodiment for imaging the mouth region 2 of the container, using a prism 45. In the illustrated example, the prism 45 is rotationally symmetrical about the axis A and is therefore cone-shaped. Refraction occurs at the faces 45' and 45", directing the ray path 44 towards the camera, which is not shown in the drawing. The lighting arrangement for illuminating the mouth region 2 of the container has again been omitted from the drawing. In the example shown in FIG. 15, correction of aberration is by means of a correction device 47 which is placed in the ray path behind the prism 45. This construction with a prism 45 also yields a simple and robust imaging arrangement for imaging the mouth region.

Figure 16:
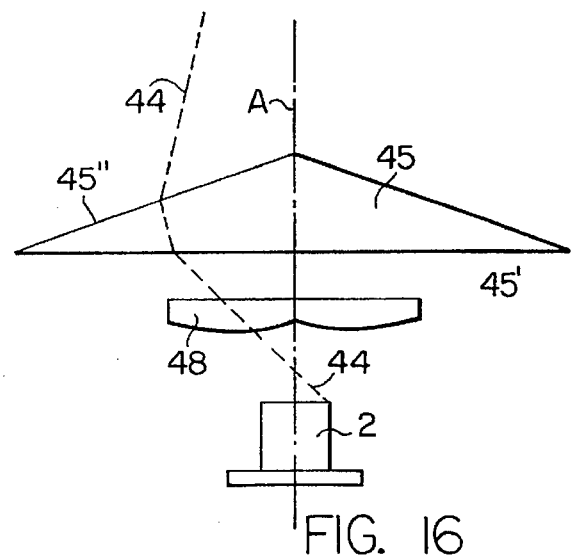
FIG. 16 shows another embodiment of the arrangement shown in FIG. 15.

FIG. 16 shows a variant of the imaging arrangement with the conical prism 45 shown in FIG. 15. In this figure, the same reference numbers denote the same elements as in FIG. 15. In this case, correction of aberration is effected by means of a lens 48 which is placed in the ray path in front of the prism.

Figure 17:
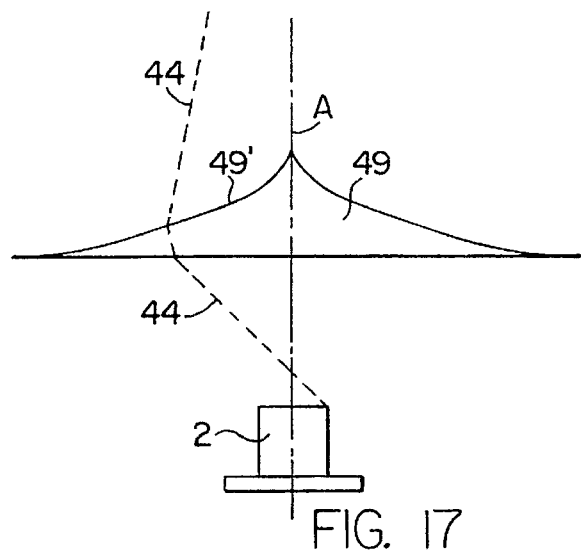
FIG. 17 shows an imaging arrangement with a one-piece curved prism.

FIG. 17 shows an imaging variant with a prism which is rotationally symmetrical about the axis A and which has a curved surface 49'.

Figure 18:
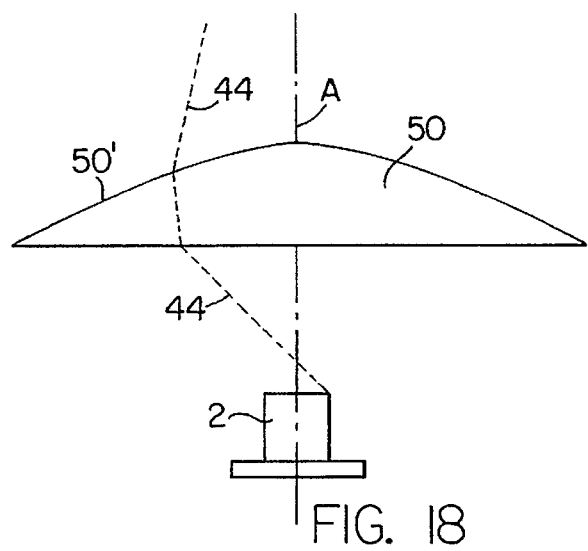
FIG. 18 shows another arrangement similar to that shown in FIG. 17.

FIG. 18 shows another embodiment with a prism 50, also with a curved surface 50' to correct aberration.

Figure 19:
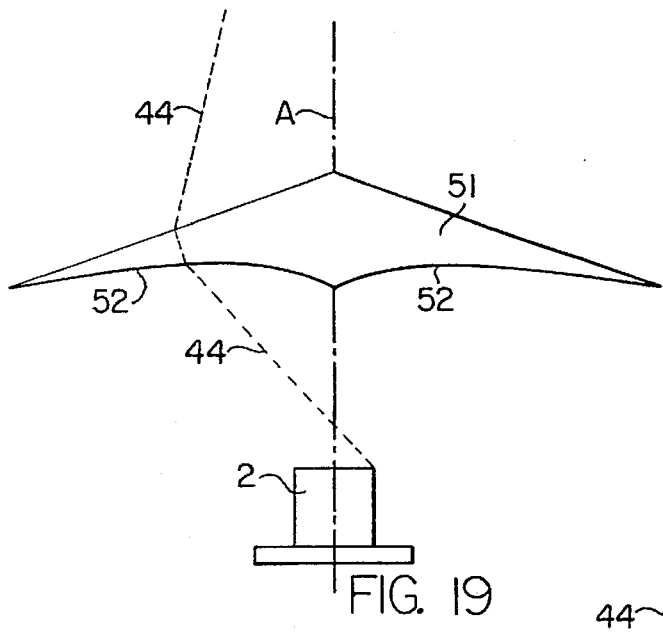
FIG. 19 shows a further embodiment for imaging by means of a prism.

FIG. 19 shows another embodiment with a prism 51 which has a surface 52 with curvature to correct aberration.

Figure 20:
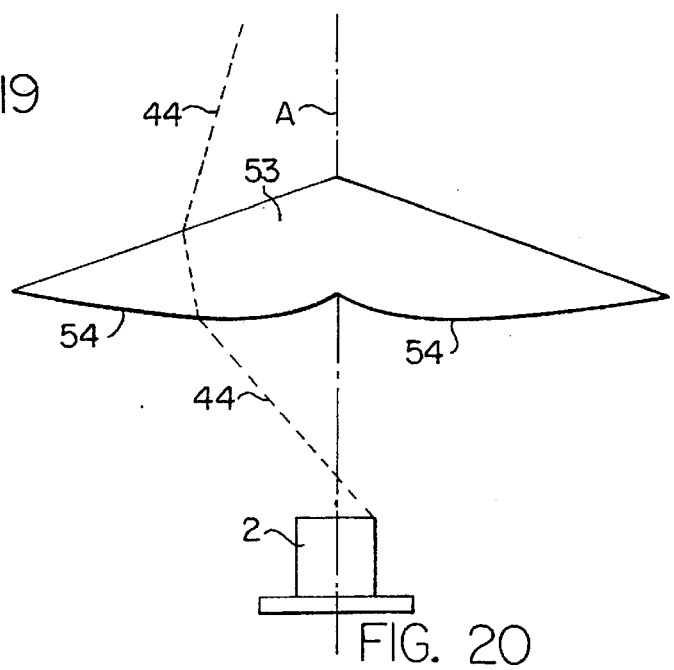
FIG. 20 shows another embodiment for imaging by means of a prism.

The same is true for the embodiment shown in FIG. 20, in which the prism 53 possesses a curved surface 54 which likewise corrects aberration due to the prism.

Figure 21:
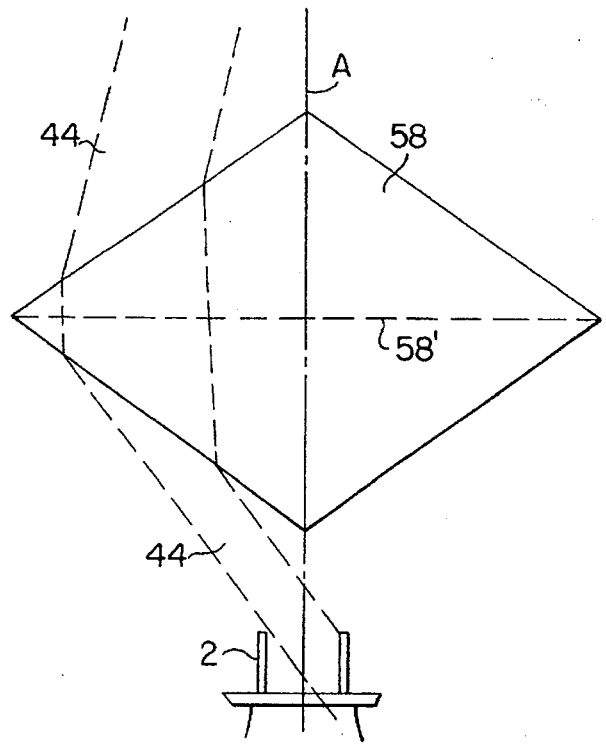
FIG. 21 shows another embodiment with a prism.

FIG. 21 shows a prism 58 which is rotationally symmetrical about the axis A. This prism can be made in one or two parts; its two-part form is indicated in the figure by the parting line 58'.

Figure 22A:
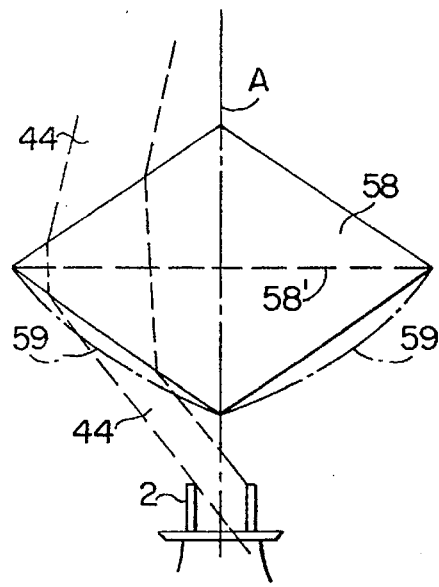
FIGS. 22a–22e show embodiments similar to that in FIG. 21, likewise with correction of aberration.
Figure 22B:
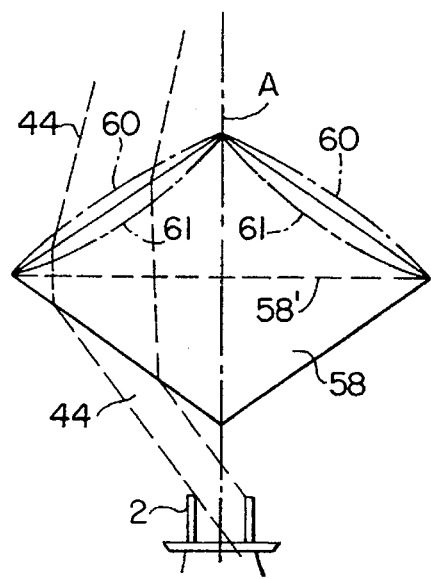
Figure 22C:
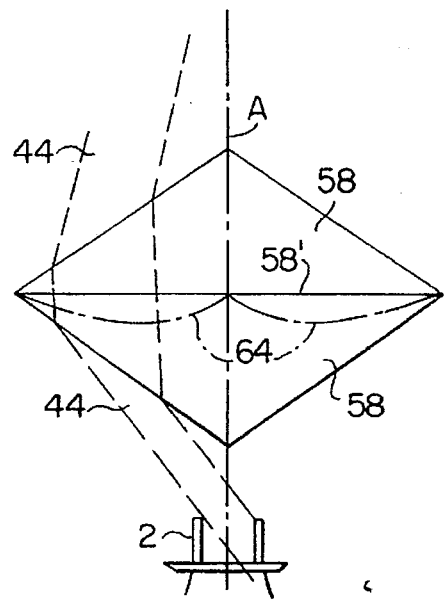
Figure 22D:
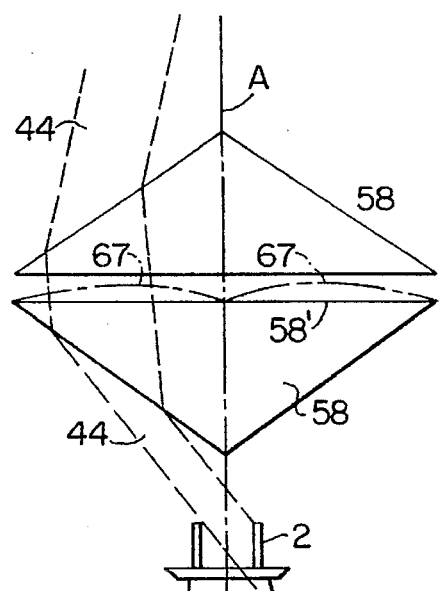

FIGS. 22a–22d show various embodiments of the prism 58 with curved surfaces to correct aberration. Thus, FIG. 22a shows a curved surface 59 on the side of the prism towards the bottle. In FIG. 22b, the curved surfaces 60 and 61 are illustrated as two alternative embodiments. FIG. 22c shows a prism 58 which has an internal curved surface 64. This prism is preferably made from two parts, as indicated by the parting line 58'. FIG. 22d likewise shows a prism 58 with an internal curved surface 67, this prism also being preferably constructed from two parts.

Figure 22E:
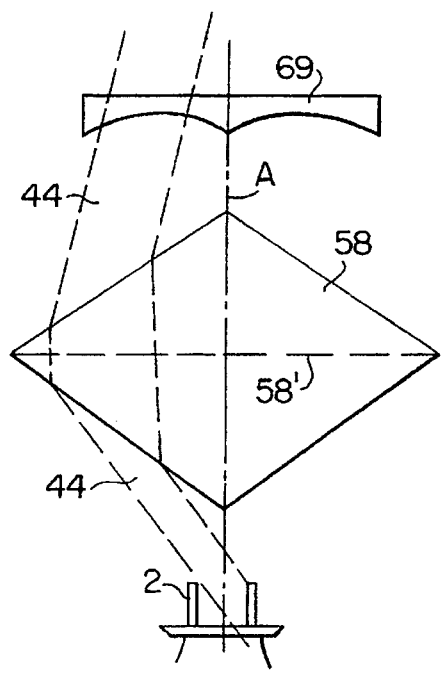

Finally, FIG. 22e shows an arrangement for imaging the mouth region 2 in which a correcting arrangement 69 is placed behind the prism 58 to correct aberration due to the prism.

The illustrated examples relate to the inspection of bottle mouths. However, it will be immediately apparent that the invention can also be used for the inspection of other kinds of container and other parts of containers. For observation by transmitted light, container regions which are at least partly transparent are, of course, necessary.

We claim:

1. Process for the optical inspection of a transparent mouth region of a bottle, comprising the steps of:

arranging at least one substantially homogeneous light-emitting surface in a substantially surrounding relationship with the container and positioned completely below the mouth region to be inspected for directing light from below the mouth region upwardly towards the mouth region and through the mouth region, directing light transmitted through and exiting from the mouth region further upwardly to at least one optical element positioned above the mouth region, and directing the transmitted light from the at least one optical element to a camera so that the mouth region can be photographed using the transmitted light.

2. Process according to claim 1, wherein the optical element includes a mirror arrangement.

3. Process according to claim 1, characterized in that imaging is performed by at least one refracting body, in particular a prism, or by at least one refracting body in combination with at least one mirror.

4. Process according to claim 1, characterized in that the image is produced by means of optical fibres.

5. Process according to claims 1, characterized in that each bottle to be inspected is surrounded, below the region, by a reflecting surface forming the light-emitting surface, the inspection stage is performed by illuminating the reflecting surface and recording the camera picture, and the reflecting surface is removed from the container.

6. Process according to claim 5, characterized in that reflecting surface for each bottle is formed by the joining of at least two parts.

7. Apparatus for optically inspecting a transparent mouth region of a container which produces an image of the region comprising:

an illuminating device for emitting light, a reflecting surface which is illuminated by and reflects light from the illuminating device and which is arranged around the container and below the region to be inspected to reflect and transmit light upwardly through the mouth region, a camera, and optical means positioned completely above the mouth region to be inspected for directing light which is transmitted from the reflecting surface and through the mouth region further upwardly to the camera so that the camera images the mouth region in transmitted light.

8. Apparatus according to claim 7, characterized in that the illuminating device is constituted by an annular array of light-emitting diodes.

9. Apparatus according to claim 7, characterized in that the reflecting surface is constituted by an internal conical surface open towards the illuminating device.

10. Apparatus according to claim 7, characterized in that in addition to the light-emitting surface a mirror surface is provided to reflect light from the container for observation.

11. Apparatus according to claim 7, characterized in that the reflecting surface is curved over at least part of its extent.

12. Apparatus for optical inspection as defined in claim 7 wherein the optical means is a prism/mirror arrangement.

13. Apparatus for optical inspection as defined in claim 7 wherein the optical means is an arrangement of optical fibers.

14. Apparatus according to claim 7, characterized by a conveyor system for conveying upright containers, a device for positioning the light-emitting surface with a container to be inspected and removing it therefrom, and an inspection apparatus comprising at least one camera for photographing the container region illuminated by the light-emitting surface.

15. Apparatus according to claim 14, characterized in that the device for positioning and removing the light-emitting surface comprises two turntables whose rotation is synchronized with the conveyor system, each carrying light-emitting segments which combine to form the light-emitting surface providing said illumination for the inspection apparatus.

16. Apparatus for optical inspection as defined in claim 7 wherein the optical means is a prism arrangement.

17. Apparatus according to one of claim 16, characterized in that the prism made in one piece or composed of several parts is provided.

18. Apparatus for optical inspection as defined in claim 7 wherein the optical means is a mirror arrangement.

19. Apparatus according to claim 18, characterized in that the mirror arrangement comprises at least one parabolic mirror.

20. Apparatus according to claim 18, characterized in that the optical means comprises a conical mirror having an external conical surface pointing towards the camera.

21. Apparatus according to claim 20, characterized in that the conical mirror is surrounded by a cylindrical mirror, and an annular mirror (6) is arranged above the cylindrical mirror.

22. Apparatus according to claim 20, characterized in that a further conical mirror is arranged above the first conical mirror.

23. Apparatus according to claim 18, characterized in that the prism/mirror arrangement comprises a rotationally symmetrical body acting as a prism, which has at least two reflecting faces.

24. Apparatus according to claim 23, characterized in that the prism is provided with at least one curved face.

25. Apparatus according to claim 23, characterized in that a correcting arrangement is provided in front of or behind the prism.

26. Process for the optical inspection of a transparent mouth region of a bottle, comprising the steps of:

emitting light rays from a location completely below the mouth region of a bottle upwardly towards and through the mouth region to be inspected, the bottle having a longitudinal axis which intersects the mouth region;

reflecting the light rays transmitted through the mouth region obliquely toward the longitudinal axis by means of a first mirror, the first mirror being symmetrical with respect to the longitudinal axis and positioned completely above the mouth region;

reflecting light rays reflected by the first mirror by means of a second mirror, the second mirror being symmetrical with respect to the longitudinal axis and positioned above the mouth region to reflect light rays from the first mirror generally along the longitudinal axis; and photographing the mouth region using the light reflected from the second mirror by means of a camera positioned on the longitudinal axis whereby the ray path, before a final reflection to the camera, extends at an oblique angle to the longitudinal axis of the container.

27. The process of according to claim 26, wherein during the steps of reflecting light, the second mirror comprises a conical mirror with its external conical surface pointing towards the camera, and the first mirror comprises a cylindrical mirror which surrounds the conical mirror and an annular mirror arranged above the cylindrical mirror.

28. The process according to claim 26, characterized in that the mirror arrangement comprises a conical mirror with its external conical surface pointing towards the camera and a mirror in the form of a frustum of a cone with its base located above the apex of the conical mirror.

29. The process according to claim 26, characterized in that the mirror arrangement comprises at least one parabolic mirror or a spherical mirror.

* * * * *